United States Patent
Popek et al.

(10) Patent No.: US 8,703,964 B2
(45) Date of Patent: *Apr. 22, 2014

(54) BENDAMUSTINE CYCLOPOLYSACCHARIDE COMPOSITIONS

(71) Applicant: Supratek Pharma Inc., Montreal (CA)

(72) Inventors: Tomasz Popek, Quebec (CA); Kishore Patel, Quebec (CA); Valery Alakhov, Quebec (CA); Grzegorz Pietrzynski, Quebec (CA)

(73) Assignee: Supratek Pharma Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/793,442

(22) Filed: Mar. 11, 2013

(65) Prior Publication Data

US 2013/0190372 A1   Jul. 25, 2013

Related U.S. Application Data

(63) Continuation of application No. 12/711,979, filed on Feb. 24, 2010, now Pat. No. 8,436,032.

(60) Provisional application No. 61/208,541, filed on Feb. 25, 2009, provisional application No. 61/269,944, filed on Jul. 1, 2009, provisional application No. 61/271,364, filed on Jul. 20, 2009, provisional application No. 61/279,293, filed on Oct. 19, 2009.

(51) Int. Cl.
*C07D 235/00* (2006.01)
*A61K 31/415* (2006.01)
*A01N 43/50* (2006.01)
*A61K 31/41* (2006.01)

(52) U.S. Cl.
USPC ............... 548/304.4; 548/302.7; 514/394; 514/385; 514/359

(58) Field of Classification Search
USPC ............ 548/304.4, 302.7; 514/393, 394, 385, 514/359
See application file for complete search history.

(56) References Cited

U.S. PATENT DOCUMENTS

| | | | |
|---|---|---|---|
| 6,407,079 | B1 | 6/2002 | Muller et al. |
| 6,583,125 | B2 | 6/2003 | Rubinfeld |
| 6,624,141 | B1 | 9/2003 | Yang et al. |
| 2006/0159713 | A1 | 7/2006 | Brittain et al. |
| 2008/0299166 | A1 | 12/2008 | Szente et al. |
| 2010/0216858 | A1 | 8/2010 | Popek et al. |

FOREIGN PATENT DOCUMENTS

| | | |
|---|---|---|
| CA | 2593582 A1 | 7/2006 |
| CA | 2593715 A1 | 8/2006 |
| CA | 2679919 A1 | 9/2008 |
| CN | 1846685 A | 10/2006 |
| CN | 101219113 A | 7/2008 |
| CN | 101606934 A | 12/2009 |

OTHER PUBLICATIONS

Chatterji et al., "Kinetick of Chlorambucil Hydrolysis Using High-Pressure Liquid Chromatography", J Pharm Sci 71 (1):50-54 (1982).
Evjen, T.J., "Developments of Improved Bendamustin-Liposomes", Thesis for the degree of Master of Pharmacy, Department of Pharmaeutics and Biopharmaceutics, Institute of Pharmacy, Faculty of Medicine, University of Tormso (2007).
Haase et al., "Untersuchungen zur Plasmaeiweiβbindung von Bendamustin (Cytostasan(R)) und Ambazon", Z. Klin. Med. 45(14):1267-1271 (1990).
Maas et al., "Stabilitat von Bendamustinhydrochlorid in Infusionsloungen", Die Pharmazie 49:775-777 (1994 ).
Meyer-Losic et al., "DTS-108, A Novel Peptidic Prodrug fo SN38; In vivo Efficacy and Toxicokinetic Studies", Clin Cancer Res 14(7):2145-2153 (2008).
Pencheva et al., HPLC Study on the stability of bendamustine hydrochloride immobilized onto polyphosphoesters, J Pharm Biomed Anal (2008) doi:10.1016/j.pba.2008.09.001.
Preiss et al., "Untersuchungen zur Pharmakokinetik von Bendamustin (Cytostasan(R)) am Menschem", Pharmazie 40:782-784 (1985).
Teichert et al., "Characterization of two phase I metabolites of bendamustine in human liver microsomes and in cancer patients treated with bendamustine hydrochloride", Cancer Chemother Pharmacol 59:759-770 (2007).
International Search Report and Written Opinion from corresponding PCT/IB2010/000502.
Wang et al., "Sulfur, oxygen, and nitrogen mustards: stability and reactivity", Org. Biomol. Chem., 2012, 10 (44):8786-8793.

*Primary Examiner* — Shirley V Gembeh
(74) *Attorney, Agent, or Firm* — Porzio, Bromberg & Newman, P.C.

(57) ABSTRACT

The present invention is directed to pharmaceutical compositions comprising: (a) bendamustine, (b) a charged cyclopolysaccharide, and (c) a stabilizing agent having a charge opposite to that of the cyclopolysaccharide. Such composition provides unexpectedly desirable stability in reactive environments such as plasma, coupled with unexpectedly desirable anticancer activity. Such compositions are suitable for injection or infusion into patients in need for treatment with bendamustine.

5 Claims, No Drawings

BENDAMUSTINE CYCLOPOLYSACCHARIDE COMPOSITIONS

CROSS REFERENCE TO RELATED APPLICATIONS

This application is a continuation of U.S. patent application Ser. No. 12/711,979, filed Feb. 24, 2010, hereby incorporated by referenced into this application. This application claims benefit under 35 U.S.C. §119(e) of U.S. Provisional Application Ser. No. 61/208,541, filed Feb. 25, 2009, U.S. Provisional Application Ser. No. 61/269,944, filed Jul. 1, 2009, U.S. Provisional Application Ser. No. 61/271,364 filed Jul. 20, 2009, and U.S. Provisional Application Ser. No. 61/279,293, filed Oct. 19, 2009, which are all herein incorporated in their entireties by reference into this application.

FIELD OF THE INVENTION

The present invention is directed to compositions of (a) bendamustine, (b) a charged cyclopolysaccharide, and (c) a stabilizing agent.

BACKGROUND OF THE INVENTION

Bendamustine, 4-[5-[bis(2-chloroethyl)amino]-1-methylbenzimidazol-2-yl]butanoic acid, is used in the treatment of leukemia and certain lymphomas. However, this compound has limited chemical stability in plasma, thereby requiring high or repeated doses in order to achieve a therapeutic effect. Thus there is a need for formulations of this drug which will exhibit increased stability.

Attempts have been made to increase the stability of bendamustine by complexing such molecule with polymeric materials. However, the approaches taken have only achieved marginal success. Thus, Pencheva et al; "HPLC study on the stability of bendamustine hydrochloride immobilized onto polyphosphoesters; J. Pharma. Biomed. Anal; (2008) attempted to improve the stability of bendamustine by complexing such compound with polyphosphoesters. However, FIG. 2 of such article shows that even the most stable complex decreases by a full log point (90%) in about 45 minutes at pH 7.

Somewhat similarly Evjen; "Development of Improved Bendamustin-Liposomes"; Masters Thesis; University of Tromso (2007) employed dual asymmetric centrifugation to incorporate bendamustine into liposomes. According to Table 18 (on page 79), these formulations only provide a marginal increase of stability relative to free bendamustine (20 minutes half-life vs. 14 minutes half-life for free bendamustine when dispersed in a cell culture medium).

Accordingly, there is a need for improved formulations of bendamustine which will provide enhanced stability in aqueous solutions, particularly plasma.

SUMMARY OF THE INVENTION

The present invention is directed to a composition comprising: (a) bendamustine, (b) a charged cyclopolysaccharide, and (c) a stabilizing agent; preferably a stabilizing agent having a charge opposite to that of the cyclopolysaccharide. Such composition provides unexpectedly desirable stability in reactive environments such as plasma, coupled with unexpectedly desirable anticancer activity. Such composition is suitable for injection or infusion into patients in need of treatment with bendamustine.

DETAILED DESCRIPTION

The present invention is directed to a composition comprising: (a) bendamustine, (b) a charged cyclopolysaccharide, and (c) a stabilizing agent having a charge opposite to that of the cyclopolysaccharide.

Preferably, the proportion of active ingredient to cyclopolysaccharide, by weight, is between about 1:12,500 and about 1:25; is more preferably between about 1:5,000 and about 1:50; is even more preferably between about 1:2,500 and about 1:75 and most preferably between about 1:1,500 and 1:100.

The stabilizing agent is typically present in a weight ratio to the cyclopolysaccharide of between about 5:1 and about 1:1000; preferably of between about 2:1 and about 1:200.

Cyclopolysaccharides

The cyclopolysaccharides which may employed in the practice of this invention include cyclodextrins, cyclomannins, cycloaltrins, cyclofructins and the like. In general, cyclopolysaccharides comprising between 6 and 8 sugar units are preferred.

Among the preferred cyclopolysaccharides which may be employed are cyclodextrins.

Cyclodextrins are cyclic oligo-1-4-alpha-D-glucopyranoses comprising at least 6 sugar units. The most widely known are cyclodextrins containing six, seven or eight sugar units. Cyclodextrins containing six sugar units are known as alpha-cyclodextrins, those containing seven sugar units are known as beta-cyclodextrins and those consisting of eight sugar units are known as gamma-cyclodextrins. Particularly preferred cyclopolysaccharides are beta-cyclodextrins.

The cyclopolysaccharides employed are modified with one or more chargeable groups. Such chargeable groups may be anionic, in which case the stabilizing agent is cationic; or such charged groups may be cationic, in which case the stabilizing agent is anionic. Preferred anionic groups include carboxyl, sulfonyl and sulphate groups; while preferred cationic groups include quarternary ammonium groups.

As employed herein the term "charged cyclopolysaccharide" refers to a cyclopolysaccharide having one or more of its hydroxyl groups substituted or replaced with a chargeable moiety. Such moiety may itself be a chargeable group (e.g., such as a sulfonyl group) or it may comprise an organic moiety (e.g., a $C_1$-$C_6$ alkyl or $C_1$-$C_6$ alkyl ether moiety) substituted with one or more chargeable moieties. Preferred substituted cyclopolysaccharides include, but are not limited to, sulfobutyl ether beta-cyclodextrin, beta-cyclodextrin substituted with 2-hydroxy-N,N,N-trimethylpropanammonium, carboxymethylated-beta-cyclodextrin, O-phosphated-beta-cyclodextrin, succinyl-(2-hydroxy)propyl-beta-cyclodextrin, sulfopropylated-beta-cyclodextrin, heptakis(6-amino-6-deoxy)beta-cyclodextrin, O-sulfated-beta-cyclodextrin, and 6-monodeoxy-6-mono(3-hydroxy)propylamino-b-cyclodextrin; with sulfobutyl ether beta-cyclodextrin being particularly preferred.

Cationic Stabilizing Agents

In those embodiments wherein the cyclopolysaccharide is modified with anionic groups, the stabilizing agent is selected from cationic agents, or from polycationic compounds. Cationic agents which may be employed include primary amines, secondary amines, tertiary amines or quaternary ammonium compounds, such as N-alkyl-N,N-dimethylamines, N-alkyl-N,N-diethylamines, N-alkyl-N—N-diethanoloamines, N-alkylmorpholine, N-alkylpiperidine, N-alkylpyrrolidine, N-alkyl-N,N,N-trimethylammonium, N,N-dialkyl-N,N-dimethylammonium, N-alkyl-N-benzyl-NN-diimethylammonium, N-alkyl-pyridinium, N-alkyl-picolinium, alkylamidomethylpyridinium, carbalkoxypyridinium, N-alkylquinolinium, N-alkylisoquinolinium, N,N-alkylmethylpyrollidinium, and 1-alkyl-2,3-dimethylimidazolium. Particularly preferred cationic adjuvants include sterically hindered tertiary amines, such as N-alkyl-N—N-diisopropylamine, N-alkylmorpholine, N-alkylpiperidine, and N-alkylpyrrolidine; and quaternary ammonium compounds such as cetylpyridinium chloride, benzyldimethyldodecylammonium chloride, dodecylpyridinium chloride, hexadecyltrimethylammonium chloride, benzyldimethyltetradecylammonium chloride, octadecyldimethylbenzylammonium chloride, and domiphen bromide.

Polycationic compounds such as oligo- or polyamines, or pegylated oligo- or polyamines may also be employed as the stabilizing agent. Preferred polycationic compounds include oligoamines such as spermine, spermidin, putrescine, and cadaverine; polyamines: such as polyethyleneimine, polyspermine, polyputrescine, and polycadaverine; and pegylated oligoamines and polyamines of the group listed above. Particularly preferred is PI2080, polyethyleneimine 2000 conjugated with PEG 8000.

One preferred class of cationic stabilizing agents are polypeptides comprising from about 5 to about 50, more preferably between about 6 and about 20, amino acids; wherein at least about 50% of such amino acids contain a positive charge. Most preferably, such charged amino acid is arginine. Particularly preferred members of this class of peptides include arginine rich peptides comprising at least one block sequence of 4 arginines. Another particularly preferred member of this class of peptides is protamine which has been digested with thermolysin (hereinafter referred to as Low Molecular Weight Protamine or "LMWP").

Hydrophobically modified oligo- or polyamines may also be employed. Preferred stabilizing agent of this type include acetyl spermine, acetyl polyspermine, acetyl polyethyleneimine, butyryl spermine, butyryl polyspermine, butyryl polyethyleneimine, lauroyl spermine, lauroyl polyspermine, lauroyl polyethyleneimine, stearoyl spermine, stearoyl polyspermine, and stearoyl polyethyleneimine, In addition, cationic polysaccharides and synthetic polycationic polymers may also be employed. Illustrative of such cationic polysaccharides are chitosan, deacetylated chitosan, quaternized cellulose, quaternized amylose, quaternized amylopectine, quaternized partially hydrolyzed cellulose, quaternized partially hydrolyzed amylose and quaternized partially hydrolyzed amylopectine. Illustrative of such synthetic polycationic polymers are Polyquaternium 2 (poly[bis(2-chloroethyl]ether-alt-1,3-bis[3-dimethylamino)propyl]-urea quaternized); Polyquaternium 11 (poly(1-vinylpyrrolidone-co-dimethylammonioethyl methacrylate) quaternized); Polyquaternium 16 and 44 (copolymer of vinylpyrrolidone and quaternized vinylimidazole); and Polyquaternium 46 (copolymer of vinylcaprolactam, vinylpyrrolidone and quaternized vinylimidazole).

Anionic Stabilizing Agents

In those embodiments wherein the cyclopolysaccharide is modified with cationic groups, the stabilizing agent is selected from anionic agents, or from polyanionic polymers. Preferably, such anionic agent is selected from compounds comprising a carboxy-, sulfate-, sulfono-, phosphate-, or phosphono-group.

One class of anionic agents that may be employed are anionic surfactants such as sodium 3[(3-cholamidopropyl)dimethylammonio]-1-propanesulfonate, sodium N-lauroyl-sarcosinate, sodium dodecyl sulfate, sodium dodecylbenzylsulfonate and the like.

Cationic polysaccharides may also be employed as the stabilizing agent. Illustrative of such compounds are chondroitin sulfate, dermatan sulphate, kappa-carrageenan, iota-carrageenan, lambda-carrageenan, mu-carrageenan, xi-carrageenan, psi-carrageenan, tau-carrageenan, furcellaran, heparan sulphate, keratin, fucoidan, hyaluronic acid, alginic acid, poly(sulfonylbutylo)cellulose, poly(sulfonylpropylo)cellulose, poly(sulfonylpropylo)dextran, poly(sulfonylbutylo)dextran, poly(sulfonylbutylo)amylase and poly(sulfonylpropylo)amylase.

The stabilizing agent may also be a polyanionic polymer selected from polyacrylates, polymethacrylates, and their copolymers.

Excipients

The compositions of this invention may further contain pharmaceutically acceptable excipients, such as sugars, polyalcohols, soluble polymers, salts and lipids.

Sugars and polyalcohols which may be employed include, without limitation, lactose, sucrose, mannitol, and sorbitol.

Illustrative of the soluble polymers which may be employed are polyoxyethylene, poloxamers, polyvinylpyrrolidone, and dextran.

Useful salts include, without limitation, sodium chloride, magnesium chloride, and calcium chloride.

Lipids which may be employed include, without limitation, fatty acids, glycerol fatty acid esters, glycolipids, and phospholipids.

Preparation

The composition of the invention may be prepared by the dissolution of solid bendamustine in an aqueous solution of the cyclopolysaccharide; or by mixing an aqueous solution of the cyclopolysaccharide with an aqueous stock solution of bendamustine. Such resulting mixture is vigorously mixed and optionally subjected to the action of ultrasound waves to obtain an homogenous and equilibrated aqueous solution. When the cyclopolysaccharide is a cyclodextrin, it is preferred that the aqueous solution of cyclodextrin used for the preparation of composition contains at least 4% of cyclodextrin; more preferably such solution contains at least 10% of cyclodextrin.

The stabilizing agent and excipient (if present) are preferably introduced to the composition by their addition to a pre-prepared aqueous homogenous and equilibrated solution of bendamustine with the cyclopolysaccharide. Such agents may be added either as pure substances or as aqueous solutions and are preferably mixed employing gentle agitation.

Preferably, the final composition is filtered before use for injection.

The composition may be optionally freeze-dried to produce a solid material suitable for dissolution in injection media before its use. It is preferred that compositions comprising amines as stabilizing agents are freeze dried prior to the addition of such stabilizing agent, with such agent being introduced into the composition after reconstitution, shortly before use.

In one embodiment the composition of this invention is prepared by mixing the components and incubation.

In another embodiment the composition of this invention is prepared by mixing the components and applying ultrasound to the mixture.

In another embodiment the composition of this invention is prepared by mixing the components, incubation, and freeze-drying the product.

In a preferred embodiment the composition of this invention is prepared by mixing the components, applying ultrasound to the mixture, and freeze-drying the product.

The compositions of this invention demonstrate enhanced stability in aqueous solution and when introduced into plasma, both under in vitro and under in vivo conditions. Thus, such formulations will exhibit a half-life in plasma which is greater than that of non-formulated bendamustine; which half-life may be extended by more than 50% and preferably more than 100%.

In addition, the compositions of this invention exhibit unexpectedly improved activity against tumors relative to compositions comprising bendamustine and a cyclopolysaccharide; as well as relative to bendamustine alone.

EXAMPLES

Example 1

Preparation of a Bendamustine Composition with Sodium Sulfobutyl Ether β-cyclodextrin and Chondroitin 6 mg of bendamustine hydrochloride were dissolved in 1 mL of 20% w/w solution of sodium sulfobutyl ether β-cyclodextrin. The solution was incubated at 20° C. for 15 minutes on ultrasonic bath and mixed with 1 mL of 25% solution of chondroitin sulfate.

Example 2

Preparation of a Bendamustine Composition with Sodium Sulfobutyl Ether β-Cyclodextrin and Poly(Sulfonylbutylo)Cellulose 6 mg of bendamustine hydrochloride are dissolved in 1 ml of 30% w/w solution of sodium sulfobutyl ether β-cyclodextrin. The solution is preincubated at 10° C. for 15 minutes on ultrasonic bath. After that the solution is mixed with 1 ml of 2% solution of poly(sulfonylbutylo)cellulose sodium salt. The sample is incubated on ultrasonic bath for 30 minutes at 10° C.

Example 3

Preparation of a Bendamustine Composition with Sodium Sulfobutyl Ether β-Cyclodextrin and Hyaluronic Acid 6 mg of bendamustine hydrochloride were dissolved in 1 mL of 30% w/w solution of sodium sulfobutyl ether β-cyclodextrin. The solution was preincubated at 10° C. for 15 minutes on ultrasonic bath. After that the solution was mixed with 1 mL of 0.1% solution of hyaluronic acid sodium salt. The sample was incubated on ultrasonic bath for 30 minutes at 10° C.

Example 4

Preparation of a Bendamustine Composition with Sodium Sulfobutyl Ether β-Cyclodextrin and Dextran 6 mg of bendamustine hydrochloride were dissolved in 1 mL of 20% w/w solution of sodium sulfobutyl ether β-cyclodextrin. The solution was incubated at 20° C. for 15 minutes on ultrasonic bath and then mixed with 1 mL of 50% solution of dextran 40 (MW 40000) and sonicated for another 15 minutes.

Example 5

Preparation of a Bendamustine Composition with 2-Hydroxypropyl-β-Cyclodextrin and Dextran 6 mg of bendamustine hydrochloride were dissolved in 1 mL of 20% w/w solution of 2-hydroxypropyl-β-cyclodextrin. The solution was incubated at 20° C. for 15 minutes on ultrasonic bath and then mixed with 1 mL of 50% solution of dextran 40 (MW 40000) and was sonicated for another 15 minutes.

Example 6

Preparation of a Bendamustine Composition with Sodium Sulfobutyl Ether β-Cyclodextrin and Quaternized Cellulose 2 mg of quaternized cellulose (hydrochloride salt) were dissolved in 1 mL of water. After 4 hours of preincubation on an ultrasonic bath (at room temperature), the solution was mixed with a solution of 6 mg of bendamustine hydrochloride in 1 mL of 20% w/w solution of sodium sulfobutyl ether β-cyclodextrin. The solution was well mixed and incubated for 15 minutes on ultrasonic bath.

Example 7

Preparation of a Bendamustine Composition with Sodium Sulfobutyl Ether β-Cyclodextrin and Polyvinylpyrrolidone 6 mg of bendamustine hydrochloride were dissolved in 1 mL of 30% w/w solution of sodium sulfobutyl ether β-cyclodextrin. The solution was incubated at 20° C. for 15 minutes on an ultrasonic bath and then mixed with 1 mL of 20% solution of PVP (MW=10000) and sonicated for 20 minutes.

Example 8

Preparation of a Bendamustine Composition with Sodium Sulfobutyl Ether β-Cyclodextrin and Cetylpyridinium Chloride 6 mg of bendamustine hydrochloride and 8.5 mg of mannitol were dissolved in 0.8 g of 50% w/w solution of sodium sulfobutyl ether β-cyclodextrin. The solution was incubated at 20° C. for 15 minutes on ultrasonic bath and then mixed with 0.2 mL of 2.5% solution of cetylpyridinium chloride.

Example 9

Preparation of Bendamustine Composition with Sodium Sulfobutyl Ether β-Cyclodextrin and PI2080

Preparation of PI2080

Polyethyleneimine (PEI, MW 2000) was purchased from Aldrich. Poly(ethylene glycol) monomethyl ether (PEG, MW 8500) was purchased from Polymer Sources Inc. PI2080, a conjugate of PEG and PEI, was prepared following the procedure described by Vinogradov S. V. et al. in Bioconjugate Chem. 1998, 9, 805-812.4 g of PEG was reacted with 1,1'-carbonyldiimidazole in 20 mL anhydrous acetonitrile. The product of the reaction was dialysed twice against water using SpectraPor 3 membrane, MWCO 3500, and freeze-dried. The freeze-dried material was dissolved in 32 mL of methanol, mixed with 2.9 g of PEI and incubated for 24 hours at 25° C.

The product was dialysed twice against water using SpectraPor 3 membrane, MWCO 3500, and the product PI2080 was freeze-dried.

Preparation of bendamustine composition with sodium sulfobutyl ether β-cyclodextrin and PI2080.

2.5 mg of bendamustine hydrochloride and 4.3 mg of mannitol were dissolved in 0.8 g of 50% w/w solution of sodium sulfobutyl ether β-cyclodextrin. The solution was incubated at 20° C. for 15 minutes on ultrasonic bath and then mixed with 0.2 mL of 5% solution of PI2080.

Example 10

Preparation of Bendamustine Composition with Sodium Sulfobutyl Ether β-Cyclodextrin and with Protamine Sulphate 2.5 mg of bendamustine hydrochloride and 4.3 mg of mannitol were dissolved in 0.800 g of 50% w/w solution of Sodium sulfobutyl ether β-cyclodextrin. Solution was shaken at 20° C. for 90 minutes and then incubated for 30 minutes in an ultrasonic bath. Then the mixture was transferred into a suspension of 30 mg of protamine sulfate in 0.163 g of water and vigorously mixed for 15 minutes.

Example 11

Pharmacokinetics of Bendamustine Dosed to Rats in Composition with Sodium Sulfobutyl Ether β-Cyclodextrin and Cetylpyridinium Chloride The Tested Compositions:
Control: 6 mg/mL bendamustine hydrochloride, 10.2 mg/mL of mannitol in 0.9% NaCl; dose of 20 mg/kg
Inventive Composition: 5 mg/g bendamustine hydrochloride, 40% w/w sodium sulfobutyl ether β-cyclodextrin, 0.5% cetylpyridinium chloride, 8.5 mg/g mannitol in water (produced following the procedure of Example 8); dose of 20 mg/kg.
Animals:
Female Sprague-Dawley rats (250-350 g). The animals were kept three per cage with an air filter cover under light (12 h light/dark cycle, light on at 06 h00) and controlled temperature 22° C.+/−1° C. All manipulations with the animals were performed under a sterilized laminar hood. The animals had ad libitum access to Purina mouse chow and water. The animals were fasted overnight and anesthetized, before dosing.
Dosing and Sampling:
The inventive bendamustine composition and control were administered intravenously to rats in tail vein. After time intervals of 5, 15, 30, 45 min, 1, 1.5, 2 and 3 hrs post-injection, blood samples were collected. The rats were anesthetized by general inhalation of isoflurane. The blood samples were collected from the jugular vein with heparinized tube and kept on ice. Blood was immediately centrifuged, and plasma was separated. The plasma samples were immediately extracted.
Sample Extraction and Analysis:
The plasma samples 0.100 mL were transferred to plastic tubes. The samples were extracted with 0.400 mL of 100 mM HCl in acetonitrile while being shaken vigorously for 30 seconds. The samples were centrifuged at 10000 RPM for 5 minutes. The supernatant was separated. The samples were frozen in dry ice and kept at −80° C. until HPLC analysis. 20 microliter aliquots were injected into the HPLC for analysis.

The HPLC Conditions:
C18 reversed phase column 50×4.6 mm, Symmetry/Shield 3.5 micrometer
Column temperature 30° C.
Flow rate 1.5 mL/min
Injection volume 20 microliters
Fluorescence detection at wavelengths: excitation 327 nm, emission 420 nm
Mobile phase: Buffer A: 5% acetonitrile 0.1% TFA
Buffer B: 90% acetonitrile 0.1% TFA
Run time: 10 min
The improved pharmacokinetic profiles of bendamustine for tested composition versus the control is shown in Table 1 below.

TABLE 1

Concentration of bendamustine in rat plasma vs. time post injection

| Time [hours] | Control [ng/mL] Mean (SEM) | Inv. Composition [ng/mL] Mean (SEM) |
|---|---|---|
| 0.08 | 12304 (2498) | 16721 (1981) |
| 0.25 | 7625 (536) | 10713 (1458) |
| 0.5 | 3046 (260) | 4855 (874) |
| 0.75 | 966 (192) | 2165 (101) |
| 1 | 414 (143) | 1108 (104) |
| 1.5 | 133 (80) | 418 (57) |
| 2 | 54 (34) | 197 (25) |
| 3 | 9 (6) | 57 (24) |

SEM—standard error of mean

The above data show that the stability of bendamustine in plasma is greatly increased in the inventive compositions of this invention.

Example 12

Pharmacokinetics of Bendamustine Dosed to Rats in Composition with Sodium Sulfobutyl Ether β-Cyclodextrin and PI2080

The Tested Compositions:
Control: 2.5 mg/mL bendamustine hydrochloride, 4.25 mg/mL of mannitol in 0.9% NaCl; dose of 10 mg/kg
Inventive Composition: 2.5 mg/mL bendamustine hydrochloride, 40% w/w sodium sulfobutyl ether β-cyclodextrin, 1% PI2080, 4.3 mg/g mannitol in water (prepared according to the procedure set forth in Example 9); dose of 10 mg/kg.
Animals:
Female Sprague-Dawley rats (250-350 g). The animals were kept three per cage with an air filter cover under light (12 h light/dark cycle, light on at 06 h00) and controlled temperature 22° C.+/−1° C. All manipulations with the animals were performed under a sterilized laminar hood. The animals had ad libitum access to Purina mouse chow and water. The animals were fasted overnight and anesthetized, before dosing.
Dosing and Sampling:
Inventive bendamustine composition and control were administered intravenously to rats in tail vein. Blood samples were collected after time intervals of 5, 15, 30, 45 min, 1, 1.5, 2 and 3 hrs post-injection, The rats were anesthetised by general inhalation of isoflurane. The blood samples were collected from the jugular vein with heparinized tube and kept on ice. The blood was immediately centrifuged, and plasma was separated. The plasma samples were immediately extracted.
Sample Extraction and Analysis:
The plasma samples 0.100 mL were transferred to plastic tubes. The samples were extracted with 0.400 mL of 100 mM HCl in acetonitrile while being shaken vigorously for 30 seconds. The samples were centrifuged at 10000 RPM for 5 minutes. The supernatant was separated. The samples were frozen in dry ice and kept at −80° C. until HPLC analysis. The aliquots of 20 microliters were injected into HPLC for analysis.

The HPLC Conditions:
C18 reversed phase column 50×4.6 mm, Symmetry/Shield 3.5 micrometer
Column temperature 30° C.
Flow rate 1.5 mL/min
Injection volume 20 microliters
Fluorescence detection at wavelengths: excitation 327 nm, emission 420 nm
Mobile phase: Buffer A: 5% acetonitrile 0.1% TFA
Buffer B: 90% acetonitrile 0.1% TFA
Run time: 10 min The improved pharmacokinetic profiles of Bendamustine for tested inventive composition versus the control is shown in Table 2 below.

TABLE 2

Concentration of bendamustine in rat plasma vs. time post injection

| Time [hours] | Control [ng/mL] Mean (SEM) | Inv. Composition [ng/mL] Mean (SEM) |
|---|---|---|
| 0.08 | 6045 (388) | 6124 (508) |
| 0.25 | 2428 (250) | 2814 (392) |
| 0.5 | 520 (105) | 1234 (92) |
| 0.75 | 145 (35) | 549 (95) |
| 1 | 48 (11) | 314 (118) |
| 1.5 | 8 (1) | 188 (97) |
| 2 | 2 (1) | 118 (60) |
| 3 | 0 (1) | 48 (23) |

SEM—standard error of mean

The above data demonstrates that the stability of bendamustine in plasma is greatly increased in the compositions of the present invention.

Example 13

Pharmacokinetics of Bendamustine Dosed to Rats in Composition with Sodium Sulfobutyl Ether β-Cyclodextrin and Protamine Sulphate the Tested Compositions:
Control: 2.5 mg/mL bendamustine hydrochloride, 4.25 mg/mL of mannitol in 0.9% NaCl; dose of 10 mg/kg
Inventive Composition: 2.5 mg/mL bendamustine hydrochloride, 40% w/w sodium sulfobutyl ether β-cyclodextrin, 3% protamine sulfate, 4.3 mg/g mannitol in water (produced according to the process described in Example 10); dose of 10 mg/kg.
Animals:
Female Sprague-Dawley rats (250-350 g). The animals were kept three per cage with an air filter cover under light (12 h light/dark cycle, light on at 06 h00) and controlled temperature of 22° C.+/−1° C. All manipulations with the animals were performed under a sterilized laminar hood. The animals had ad libitum access to Purina mouse chow and water. The animals were fasted overnight and anesthetized, before dosing.
Dosing and Sampling:
Bendamustine composition and control were administered intravenously to rats in tail vein. After time intervals 5, 15, 30, 45 min, 1, 1.5, 2 and 3 hrs post-injection, the blood samples were collected. The rats were anesthetized by general inhalation of isoflurane. The blood samples were collected from the jugular vein with heparinized tube and kept on ice. Blood was immediately centrifuged, and plasma was separated. The plasma samples were immediately extracted.
Sample Extraction and Analysis:
The plasma samples 0.100 mL were transferred to plastic tubes. The samples were extracted with 0.400 mL of 100 mM HCl in acetonitrile while being shaken vigorously for 30 seconds. The samples were centrifuged at 10000 RPM for 5 minutes. The supernatant was separated. The samples were frozen in dry ice and kept at −80° C. until HPLC analysis. 20 microliter aliquots were injected into HPLC for analysis.

The HPLC conditions:
C18 reversed phase column 50×4.6 mm, Symmetry/Shield 3.5 micrometer
Column temperature 30° C.
Flow rate 1.5 mL/min
Injection volume 20 microliters
Fluorescence detection at wavelengths: excitation 327 nm, emission 420 nm
Mobile phase: Buffer A: 5% acetonitrile 0.1% TFA
Buffer B: 90% acetonitrile 0.1% TFA
Run time: 10 min The improved pharmacokinetic profiles of Bendamustine for tested composition versus the control is shown in Table 3 below.

TABLE 3

Concentration of bendamustine in rat plasma vs. time post injection

| Time [hours] | Control [ng/mL] Mean (SEM) | Inv. Composition [ng/mL] Mean (SEM) |
|---|---|---|
| 0.08 | 6045 (388) | 3853 (787) |
| 0.25 | 2428 (250) | 2416 (716) |
| 0.5 | 520 (105) | 1100 (313) |
| 0.75 | 145 (35) | 595 (154) |
| 1 | 48 (11) | 415 (140) |
| 1.5 | 8 (1) | 139 (20) |
| 2 | 2 (1) | 126 (36) |
| 3 | 0 (0) | 47 (18) |
| 4 |  | 19 (9) |

SEM—standard error of mean

The above data shows that the stability of the cyclopolysaccharide composition is greatly increased when compared to that of bendamustine alone.

Example 14

Preparation of Bendamustine Composition with Sodium Sulfobutyl Ether β-Cyclodextrin and Luviquat FC370

6 mg of bendamustine hydrochloride was dissolved in 1 mL of 30% w/w solution of sodium sulfobutyl ether β-cyclodextrin. The solution was preincubated at 10° C. for 15 minutes on ultrasonic bath; and then mixed with 1 mL of 0.1% solution of Luviquat FC370.

Luviquat FC370 (Polyquaternium-16) is a copolymer of vinylpyrrolidone and quaternized vinylimidazole (CAS No. 95144-24-4 (BASF). The sample was incubated on ultrasonic bath for 30 minutes at 10° C.

Example 15

Preparation of Bendamustine Composition with Sodium Sulfobutyl Ether β-Cyclodextrin and Luviquat HOLD 6 mg of bendamustine hydrochloride were dissolved in 1 mL of 30% w/w solution of sodium sulfobutyl ether β-cyclodextrin. The solution was preincubated at 10° C. for 20 minutes in an ultrasonic bath; and then mixed with 1 mL of 0.15% solution of Luviquat HOLD. Luviquat HOLD (Polyquaternium-46) is 1H-imidazolium, 1-ethenyl-3-methyl-methyl sulphate polymer with 1-ethenylhexahydro-2Hazepin-2-one and 1-ethenyl-2-pyrrolidinone, CAS No. 174761-16-1, (BASF). The sample was incubated in an ultrasonic bath for 30 minutes at 10° C.

Example 16

Preparation of Bendamustine Composition with Sodium Sulfobutyl Ether β-Cyclodextrin and Quaternized Poly(Vinylpyrrolidone-co-2-Dimethylaminoethyl Methacrylate)

6 mg of bendamustine hydrochloride were dissolved in 1 mL of 30% w/w solution of sodium sulfobutyl ether β-cyclodextrin. The solution was preincubated at 10° C. for 15 minutes in an ultrasonic bath. After that the solution was mixed with 1 mL of 0.1% solution of quaternized poly(vinylpyrrolidone-co-2-dimethylaminoethyl methacrylate). The sample was incubated in an ultrasonic bath for 30 minutes at 10° C.

Example 17

Preparation of a Bendamustine Composition with Sodium Sulfobutyl Ether β-Cyclodextrin and Quaternized Poly(Vinylpyrrolidone-co--Dimethylaminoethyl Methacrylate)

6 mg of bendamustine hydrochloride were dissolved in 1 mL of 30% w/w solution of sodium sulfobutyl ether β-cyclodextrin. The solution was preincubated at 10° C. for 15 minutes in an ultrasonic bath. After that the solution was mixed with 1 mL of 0.1% solution of quaternized poly(vinylpyrrolidone-co-2-dimethylaminoethyl methacrylate). The sample was incubated in an ultrasonic bath for 30 minutes at 10° C.

Example 18

Preparation of Bendamustine Composition with Sodium Sulfobutyl Ether β-Cyclodextrin and Chitosan 5 mg of low-weight chitosan were suspended in 5 mL of 0.2M chydrochloric acid and mixed overnight. The content of the vial was filtered through a 0.45 um glass fiber filter and lyophilized. 2 mL of a 30% w/w solution of sodium sulfobutyl ether β-cyclodextrin were added to the lyophilized material. The mixture was incubated at 20° C. for 24 hours and filtered through a 0.45 um glass fiber filter. 1 mL of said solution was used to dissolve 6 mg of bendamustine hydrochloride. The solution was incubated at 10° C. for 20 minutes in an ultrasonic bath.

Example 19

Preparation of Bendamustine Composition with Sodium Sulfobutyl Ether β-cyclodextrin and Quaternized poly(bis(2-chloroethyl)ether-alt-1,3-bis[3-dimethylamino)propyl]-urea 6 mg of bendamustine hydrochloride were dissolved in 1 mL of a 30% w/w solution of sodium sulfobutyl ether β-cyclodextrin. The solution was preincubated at 10° C. for 15 minutes in an ultrasonic bath. After that the solution was mixed with 1 mL of a 0.05% solution of quaternized poly(bis(2-chloroethyl)ether-alt-1,3-bis[3-dimethylamino)propyl]-urea. The sample was incubated in an ultrasonic bath for 30 minutes at 10° C.

Example 20 a. Preparation of Low Molecular Weight Protamine (LMWP)

2 g of protamine sulfate were dissolved in 70 mL 0.1 M ammonium acetate buffer, pH 7 to form a protamine sulphate solution. 20 mg of thermolysin were dissolved in 10 mL 50 mM Tris buffer, pH 7.4 to form a thermolysin solution. The thermolysin solution was added to the protamine sulfate solution, followed by 70 microliters of 1 M aqueous calcium chloride. The mixture was incubated for 30 minutes at room temperature. 0.7 mL 0.7 M EDTA solution was added to the mixture. The mixture was lyophilized. The dry material was redissolved in 0.2% aqueous acetic acid, 100 mg per 1 mL and filtered through 0.22 micrometer filter. 5 mL of the solution was injected into RP-HPLC column Vaydac 218TP152050, 5×25 cm. The sample was eluted with gradient ethanol in water comprising 0.2% acetic acid. The fraction containing the product was collected and lyophilized.

b. Preparation of Bendamustine Composition with Sodium Sulfobutyl Ether β-Cyclodextrin ("SBECD") and Low Molecular Weight Protamine ("LMWP")

400 mg of sodium sulfobutyl ether β-cyclodextrin were mixed with 0.600 mL of water and shaken until completely dissolved. 16 mg of bendamustine hydrochloride and 27.3 mg of mannitol were added to this solution and shaken for 90 minutes. 20 mg of LMWP were dissolved in 936.8 mg of water, and mixed with the bendamustine solution. The product was stored at 4° C. The product was assessed for bendamustine content using analytical RP-HPLC chromatography as follows. 10 μL samples were separated using Waters SymmetryShield RP-18 3.5 μm column (4.6×50 mm) at the flow of 1.5 mL/min of acetonitrile-water gradient containing 0.1% TFA. Peak detection has been performed by means of UV absorption detection at 260 nm. The area of the peak of bendamustine was used to evaluate the rate of drug stability, in triplicates. The area under the peak of bendamustine after 24 hours was 101.8% of the initial (standard deviation 2%).

Example 21

Preparation of Lyophilised Bendamustine Composition with Sodium Sulfobutyl Ether β-Cyclodextrin and Low Molecular Weight Protamine

The composition of Example 20 was lyophilised. The product was amorphous white solid, soluble in water. The product before use was reconstituted with 1.536 mL of water.

Example 22

Cytotoxicity of Bendamustine Compositions

H460, RPMI8226, and MDA-MB-231 cells were maintained in appropriate medium, containing 10% foetal bovine serum (FBS) and antibiotics. 24 h after plating bendamustine (BM); BM in the presence of 0.1% sodium sulfobutyl ether β-cyclodextrin (SBECD): and BM in the presence of 0.1% SBECD and 0.002-0.005% low molecular weight protamine (LMWP) were added in different concentrations to cell cultures and cells were grown for three days. The drug cytotoxicity was evaluated using WST-1 procedure.

IC50 values were estimated for bendamustine, bendamustine formulated in SBECD, and bendamustine formulated in SBECD/LMWP. Table 4 shows the increase in BM potency produced by formulation of the drug in SBECD or SBECD/LMWP. As a measure of change in BM cytotoxic activity the ratios of BM IC50 to IC50 of BM in SBECD or SBECD/LMWP formulation were calculated. For each cell line, these ratios represent averages for 3-12 independent experiments.

TABLE 4

Increase in BM potency (BM IC50/formulation IC50, in parentheses standard error).

| Composition | Cell line | | |
|---|---|---|---|
| | H460 | RPMI8226 | MDA-MB-231 |
| BM | 1.0 | 1.0 | 1.0 |
| BM + SBECD | 1.2 (0.2) | 1.6 (0.1) | 1.6 (0.5) |
| BM + SBECD + LMWP | 1.9 (0.3) | 2.5 (0.4) | 2.2 (0.1) |

SBECD formulation increased potency of BM, decreasing its IC50. Addition of LMWP to SBECD formulation further substantially decreased BM IC50. In two cell lines, H460 and RPMI8226, effect of LMWP was statistically significant, $p=0.036$ and 0.018, respectively. In MDA-MB-231 cells effects of both formulations were not significantly different. For these three cell lines, average decrease in IC50 of BM was 1.5- and 2.2-fold for SBECD and SBECD/LMWP, respectively.

Example 23

Cytotoxicity of Bendamustine Compositions Pre-Incubated with Media

BM and SBECD/LMWP formulation (40 mg/ml BM in 20% SBECD, 1% LMWP) were incubated in DMEM medium containing 10% FBS for 0, 1, or 4 h and then were added in varying concentrations to RPMI8226 cells. During BM treatment, concentrations of SBECD and LMWP were kept constant in culture medium at 0.1 and 0.05%, respectively. Cells were then grown for 72 h. The drug cytotoxicity was evaluated using WST-1 procedure. The results are presented in Tables 5 and 6 below.

TABLE 5

Cell growth of RPMI8226 cells treated with bendamustine, pre-incubated in cell culture medium for 0, 1, or 4 h.

| Bendamustine, uM | BM 0 h | BM 1 h | BM 4 h |
|---|---|---|---|
| | | Cell growth, % | |
| 1 | 100 | 100 | 100 |
| 15 | 83 | 100 | 100 |
| 31 | 70 | 100 | 100 |
| 62 | 46 | 106 | 104 |
| 125 | 11 | 20 | 105 |
| 250 | −23 | −45 | 75 |
| 500 | −87 | −85 | 8 |
| 1000 | −98 | −102 | −99 |

TABLE 6

Cell growth of RPMI8226 cells treated with SBECD/LMWP formulation of bendamustine, pre-incubated in cell culture medium for 0, 1, or 4 h.

| Bendamustine, uM | BM/SBECD/ LMWP 0 h | BM/SBECD/ LMWP 1 h | BM/SBECD/ LMWP 4 h |
|---|---|---|---|
| | | Cell growth, % | |
| 1 | 100 | 100 | 100 |
| 15 | 71 | 71 | 114 |
| 31 | 35 | 37 | 51 |
| 62 | 21 | 39 | 29 |
| 125 | −14 | −25 | 8 |
| 250 | −99 | −98 | −104 |
| 500 | −99 | −98 | −101 |
| 1000 | −96 | −98 | −108 |

TABLE 7

IC50 of bendamustine and BM/SBECD/LMWP formulation, pre-incubated in cell culture medium for 0, 1, or 4 h, in RPMI8226 cells.

| Time of pre-incubation, h | IC50 of bendamustine, uM | |
|---|---|---|
| | BM | BM/SBECD/LMWP |
| 0 | 62 | 32 |
| 1 | 106 | 38 |
| 4 | 390 | 53 |

IC50, TGI, and LC50 parameters were calculated for each time of pre-incubation.

| | IC50, μM/h | TGI, μM/h | LC50, μM/h |
|---|---|---|---|
| BM | 85 +/− 10 | 98 +/− 18 | 107 +/− 11 |
| SBECD/LMWP formulation | 5.2 +/− 0.2 | 6.0 +/− 0.1 | 3.5 +/− 0.9 |

Where:
IC50 - concentration of a drug that causes 50% growth inhibition of cells;
TGI - concentration of a drug that causes total growth inhibition of cells;
LC50 - concentration of a drug that causes 50% death of cells.

The results show that the composition of BM, SBECD and LMWP retains potency longer than BM alone.

Example 24

Cytotoxicity of Bendamustine Composition Comprising SBECD and LMWP

RPMI8226, H69, MDA-MB-231, and H460 cells were maintained in appropriate medium, containing 10% FBS and antibiotics. 24 h after plating, bendamustine, and bendamustine formulated in SBECD/LMWP (40 mg/ml BM in 20% SBECD, 1% LMWP) were added in different concentrations to cell cultures and cells were grown for three days. The drug cytotoxicity was evaluated using WST-1 procedure. The results are presented in the Table 8 below.

TABLE 8

| Cell Line | BM | SBECD/LMWP |
|---|---|---|
| RPMI8226 | 117 | 61 |
| H69 | 254 | 119 |
| H460 | 601 | 228 |
| MDA-MB-231 | 600 | 321 |

The above data shows that the compositions of this invention possess enhanced cytotoxicity.

Example 25

Pharmacokinetics of Bendamustine Dosed to Rats in Composition with Sodium Sulfobutyl Ether β-Cyclodextrin and Low Molecular Weight Protamine (LMWP)

The following compositions were prepared for testing:
Control: 5 mg/mL bendamustine hydrochloride, 10.2 mg/mL of mannitol in 0.9% NaCl; dose of 10 mg/kg
Composition 25A
  5 mg/mL bendamustine hydrochloride, 20% w/w sodium sulfobutyl ether β-cyclodextrin, 10.2 mg/g mannitol in water; dose of 10 mg/kg.
Composition 25 B
  5 mg/mL bendamustine hydrochloride, 20% w/w sodium sulfobutyl ether β-cyclodextrin, 1% LMWP, 10.2 mg/g mannitol in water; dose of 10 mg/kg.
Animals:
Female Sprague-Dawley rats (250-350 g). The animals were kept three per cage with an air filter cover under light (12 h light/dark cycle, light on at 06 h00) and controlled temperature 22° C.+/−1° C. All manipulations with the animals were performed under a sterilized laminar hood. The animals had ad libitum access to Purina mouse chow and water. The animals were fasted overnight and anesthetized, before dosing.
Dosing and Sampling:
The bendamustine compositions and control were administered intravenously to rats via a tail vein. Blood samples were collected 5, 15, 30, 45 min, 1, 1.5, 2, 3 and 4 hrs post-injection. The rats were anesthetized by general inhalation of isoflurane. The blood samples were collected from the jugular vein with a heparinized tube and kept on ice. The sample was immediately centrifuged, and the plasma separated. The plasma samples were immediately extracted.
Sample Extraction and Analysis:
The plasma samples 0.100 mL were transferred to plastic tubes. The samples were extracted with 0.400 mL of 100 mM HCl in acetonitrile while being shaken vigorously for 30 seconds. The samples were centrifuged at 10000 RPM for 5 minutes. The supernatant was separated. The samples were frozen in dry ice and kept at −80° C. until HPLC analysis. The aliquots of 20 microliters were injected into HPLC for analysis.
The HPLC Conditions:
C18 reversed phase column 50×4.6 mm, Symmetry/Shield 3.5 micrometer
Column temperature 30° C.
Flow rate 1.5 mL/min
Injection volume 20 microliters
Fluorescence detection at wavelengths: excitation 327 nm, emission 420 nm
Mobile phase: Buffer A: 5% acetonitrile 0.1% TFA
Buffer B: 90% acetonitrile 0.1% TFA
Run time: 10 min
The pharmacokinetic profiles of Bendamustine for tested composition versus the control is shown in Table 9 below.

TABLE 9

Concentration of bendamustine in rat plasma vs. time post injection

| Time [hours] | Control [ng/mL] Mean (SEM) | Composition 25A [ng/mL] Mean (SEM) | Composition 25B [ng/mL] Mean (SEM) |
|---|---|---|---|
| 0.08 | 6045 (388) | 5233 (143) | 3629 (1286) |
| 0.25 | 2428 (250) | 1702 (217) | 1915 (708) |
| 0.5 | 520 (105) | 307 (73) | 852 (251) |
| 0.75 | 145 (35) | 72 (25) | 468 (80) |
| 1 | 47 (11) | 36 (17) | 317 (53) |
| 1.5 | 8 (1) | 16 (10) | 160 (32) |
| 2 | 2 (1) | 5 (4) | 93 (27) |
| 3 | 0 (0) | 0 (0) | 47 (20) |
| 4 | | | 12 (5) |

SEM—standard error of mean

The example shows that the presence of LMWP in Bendamustine composition with SBECD considerably increased the half-life time of BM in plasma.

Example 26

Efficacy of Bendamustine Compositions on Murine Experimental Lung Metastasis Model Animals
Female Charles Rivers C57Bl/6 mice, aged 5 to 6 weeks, were purchased from Charles River Canada Inc. The animals were kept 5 per cage with an air filter cover under light (12 light/dark cycle, light on at 6H00) and temperature (22°±1° C.)-controlled environment. All manipulations of animals were performed under a sterilized laminar hood. The animals had ad libitum access to Purina mouse chow (Pro Lab PMH 4018, Trademark of Agway, Syracuse, N.Y.) and water. These animal studies were conducted according to the "Guidelines for Care and Use of Experimental Animals".
Tumor Cell Culture:
  Lewis Lung carcinoma 3LL cells were cultured in the appropriated culture medium. The cells were harvested in their logarithmic growth phase for the preparation of tumor implantation.
Tumor Implantation:
Lewis Lung carcinoma 3LL cells (2.0 to 5.0×105 cells in 200 ul PBS) were implanted intravenously by tail vein to establish experimental lung metastasis tumor models.
Treatments:
The treatments were performed on day after tumor implantation. The animals were dosed with the following dosing solutions.
Control: (0.9%, NaCl)
Compositions:
  non-formulated bendamustine (BM), (50 mg/kg)
  Bendamustine (50 mg/kg) in 20% SBECD, 1% LMWP
Efficacy Evaluation:
Metastasis formation was evaluated by counting the numbers of metastasis spots on the lung surface. Routine metastasis examination were done for all organs at the end of the study.

The results of efficacy evaluation are presented in Table 10 below.

TABLE 10

| Treatment | Lung metastasis number (animal number) | Inhibition on metastasis formation vs control, (%) | Inhibition on metastasis formation vs not formulated BM (%) |
|---|---|---|---|
| Control | 65.5 ± 7.8 (8) | 0 | — |
| BM (50 mg/kg) | 56.1 ± 9.5 (9) | 14.4 | 0 |
| BM (50 mg/kg), 20% SBECD, 1% LMWP | 37.0 ± 8.1 (9) | 43.5 ** | 34.0 * |

** Statistically significant, p < 0.01
* Statistically significant, p < 0.05

The results show statistically significant improvement of efficacy of the composition comprising SBECD and LMWP vs. non-formulated drug.

Example 27

Efficacy of Bendamustine Compositions on Human Breast Carcinoma (MDA-MB 231) Subcutaneous (s.c.) Solid Tumours in Nude Mice Animal:
balb/c mice aged 5 to 6 weeks were purchased from Charles River Canada Inc. The animals were kept 5 per cage with an air filter cover under light (12 light/dark cycle, light on at 6 H00) and temperature (22° C.±1° C.)-controlled environment. All manipulations of animals were performed under a sterilized laminar hood. The animals had ad libitum access to Purina mouse chow (Pro Lab PMH 4018, Trademark of Agway, Syracuse, N.Y.) and water. These animal studies were conducted according to the "Guidelines for Care and Use of Experimental Animals".
Tumor Cell Culture:
Human breast cancer cells MDA-MB 231 were cultured in the appropriated culture medium. The cells were harvested in their logarithmic growth phase for the preparation of tumor implantation.
Tumor Implantation:
Human tumor or myeloma cells (2.5 to 5.0×10$^6$ cells) were implanted subcutaneously in 0.200 mL of medium containing 30% Matrigel on the two flanks of balb/c nu/nu mice through a 1 to 2 cm long 20-gauge needle.

Treatments:
2 to 3 weeks after tumor cell implantation, animals that developed s.c. solid tumors were selected and divided into several homogeneous groups (n=5 animals per group or dose) with respect to tumor size (0.5 to 0.8 cm in diameter). The treatments were performed next day. The animals were dosed with the following dosing solutions.
Control: (0.9%, NaCl)
Compositions:
  non-formulated Bendamustine, (35 mg/kg)
  Bendamustine (35 mg/kg) in 40% SBECD, 1% protamine sulfate (formulated BM)
Efficacy Evaluation:
Subcutaneous solid tumor measurements were performed on the day of first injection and at 3- to 4-day intervals thereafter. The two largest perpendicular diameters of each tumor were measured with calipers and tumor sizes were estimated using the formula:

$$TV = L \times W/2$$

where TV: tumor volume; L: length; W: width.
The body weights of animals were also noted.
The results are presented in Table 11 below.

TABLE 11

| Groups (number of animals) | Body weight on day 14 (g) | Tumor volume on day 14 (g) (number of tumors) | Inhibition % vs control (on day 14) | Remarks |
|---|---|---|---|---|
| Control (0.9%, NaCl) (5) | 19.9 ± 0.35 (4) | 1.80 ± 0.19 (8) | — | 1 of 5 dead on day 11 due to tumor metastasis. All animals were sacrificed on day 14 due to protocol limit points with tumor size. |
| BM (35 mg/kg) (5) | 18.1 ± 0.39 (5) | 0.54 ± 0.06 (10) | 70.2% | |
| BM (35 mg/kg), 40% SBECD, 1% PS (5) | 18.6 ± 0.30 (2) | 0.32 ± 0.09 (4) | 82.0% | 3 of 5 mice were dead on day 4 after treatments. |

Table 12 shows the effect of BM and its compositions on the growth of tumors.

TABLE 12

Tumor weight after treatment in human breast carcinoma MDA-MB 231 s.c. solid tumors in nude mice

| Time [days] | Non-treated Control [g] Average (SEM) | BM (35 mg/kg) [g] Average (SEM) | BM (35 mg/kg), 40% SBECD, 1% PS [g] Average (SEM) |
|---|---|---|---|
| 0 | 0.277 (0.031) | 0.237 (0.008) | 0.247 (0.012) |
| 2 | 0.329 (0.034) | 0.250 (0.028) | 0.242 (0.039) |
| 4 | 0.436 (0.052) | 0.294 (0.027) | 0.151 (0.045) |
| 7 | 0.615 (0.065) | 0.313 (0.030) | 0.182 (0.046) |
| 9 | 0.838 (0.095) | 0.349 (0.038) | 0.216 (0.046) |
| 11 | 1.164 (0.149) | 0.417 (0.046) | 0.232 (0.065) |
| 14 | 1.803 (0.185) | 0.537 (0.055) | 0.324 (0.092) |

SEM—standard error of mean

The results show unexpected toxicity and good efficacy of the composition comprising SBECD and protamine sulfate.

Example 28

Efficacy of Bendamustine Compositions on Human Breast Carcinoma MDA-MB 231 s.c. Solid Tumors in Nude Mice The experiment was performed as described in example 27, using the following compositions for treatment:
Control: (0.9%, NaCl)
Compositions:
 non-formulated bendamustine, (30 mg/kg)
 Bendamustine (30 mg/kg) in 40% SBECD (formulated BM)
The treatment was performed on days 1, 2, 9, and 10.
The results are presented in Table 13.

TABLE 13

| Groups (number of animals) | Treatment Schedules | Tumor weight on day 19 estimated from measurements of the tumor size (g) (number of tumors) | Real Tumor weight on day 19 in autopsy (g) (number of tumors) |
| --- | --- | --- | --- |
| G1. Control (0.9%, NaCl) (5) | Day 1, 2, 9, 10 | 1.70 ± 0.15 (10) | 0.855 ± 0.105 (10) |
| G2. BM (30 mg/kg) (5) | Day 1, 2, 9, 10 | 0.684 ± 0.10 (10) | 0.275 ± 0.052 (10) |
| G3. BM (30 mg/kg), 40% SBECD (5) | Day 1, 2, 9, 10 | 1.05 ± 0.18 (10) | 0.413 ± 0.067 (10) |

Table 14 shows the effect of BM and its compositions on the growth of tumors.

TABLE 14

Tumor weight after treatment in human breast carcinoma MDA-MB 231 s.c. solid tumors in nude mice

| Time [days] | Non-treated Control [g] Average (SEM) | BM (30 mg/kg) [g] Average (SEM) | BM (30 mg/kg), 40% SBECD, [g] Average (SEM) |
| --- | --- | --- | --- |
| 0 | 0.252 (0.020) | 0.203 (0.028) | 0.200 (0.024) |
| 2 | 0.288 (0.019) | 0.238 (0.023) | 0.245 (0.022) |
| 5 | 0.384 (0.029) | 0.267 (0.022) | 0.300 (0.027) |
| 7 | 0.536 (0.028) | 0.313 (0.028) | 0.392 (0.038) |
| 9 | 0.693 (0.044) | 0.388 (0.045) | 0.522 (0.060) |
| 12 | 1.034 (0.049) | 0.497 (0.060) | 0.641 (0.071) |
| 14 | 1.174 (0.065) | 0.550 (0.075) | 0.756 (0.090) |
| 16 | 1.456 (0.104) | 0.594 (0.084) | 0.853 (0.125) |
| 19 | 1.704 (0.145) | 0.684 (0.098) | 1.051 (0.176) |

SEM—standard error of mean

The above data shows that a two component system comprising bendamustine and a charged cyclodextrin (without an oppositely charged stabilizing agent) is less than that of bendamustine alone.

Example 29

Efficacy of Bendamustine Compositions on Human Breast Carcinoma MDA-MB 231 s.c. Solid Tumors in Nude Mice The experiment was performed employing the procedures described in Example 28, using the following compositions for treatment:
Control: (0.9%, NaCl)
Compositions:
 non-formulated Bendamustine, (30 mg/kg)
 Bendamustine (30 mg/kg) in 20% SBECD, 1% LMWP (formulated BM)
The treatment was performed on days 1, 2, 9, and 10.
The results are presented in Table 15.

TABLE 15

| Groups (animal number) | Treatment Schedules | Tumor weight on day 16 (g) (number of tumors) | Inhibition % vs control (on day 16) |
| --- | --- | --- | --- |
| G1. Control (0.9%, NaCl) (6) | Day 1, 2, 9, 10 | 0.789 ± 0.056 (6) | — |
| G2. BM (30 mg/kg) (6) | Day 1, 2, 9, 10 | 0.487 ± 0.067 (6) | 38.3 |
| G3. BM (30 mg/kg), 20% SBECD, 1% LMWP (6) | Day 1, 2, 9, 10 | 0.364 ± 0.028 (6) | 53.9 |

Note.
The tumors implanted in the left flank were much smaller than those in the right flank due to the lower number of tumor cells inoculated. The volume of these tumors is not included in the data presented.

Note. The tumors implanted in the left flank were much smaller than those in the right flank due to the lower number of tumor cells inoculated. The volume of these tumors is not included in the data presented.
The results show that Bendamustine composition with 20% SBECD and 1% LMWP is more active than non-formulated drug—a result which is unexpected in view of the results obtained in Example 28 above.

TABLE 16

Tumor weight after treatment in human breast carcinoma MDA-MB 231 s.c. solid tumors in nude mice

| Time [days] | Non-treated Control [g] Average (SEM) | BM (30 mg/kg) [g] Average (SEM) | BM (30 mg/kg), 20% SBECD, 1% LMWP [g] Average (SEM) |
| --- | --- | --- | --- |
| 0 | 0.161 (0.007) | 0.139 (0.013) | 0.140 (0.018) |
| 2 | 0.187 (0.011) | 0.178 (0.027) | 0.163 (0.016) |
| 4 | 0.233 (0.024) | 0.202 (0.039) | 0.167 (0.016) |
| 6 | 0.288 (0.036) | 0.259 (0.049) | 0.188 (0.010) |
| 8 | 0.344 (0.027) | 0.295 (0.054) | 0.216 (0.014) |
| 10 | 0.422 (0.031) | 0.319 (0.044) | 0.234 (0.013) |
| 12 | 0.508 (0.041) | 0.361 (0.050) | 0.258 (0.012) |
| 14 | 0.589 (0.057) | 0.417 (0.054) | 0.319 (0.022) |
| 16 | 0.789 (0.056) | 0.487 (0.067) | 0.364 (0.028) |

SEM—standard error of mean

Example 30

Bendamustin Chemical Stability in Compositions with Sulfobutyl Beta Cyclodextrin (SBECD) and Low Molecular Weight Protamine (LMWP) in Phosphate Buffer 4% SBECD (w/w) in phosphate buffer (SBECD/PB) was prepared by dissolving SBECD in 5 mM phosphate buffer and adjusting pH to 7.2.
The following compositions were prepared and tested:
Control: 0.6 mg/mL Bendamustine Hydrochloride (BM) in water, prepared by dissolving BM in 5 mM phosphate buffer (PB) pH 7.2
Composition 30-1: 0.6 mg/mL BM in 4% SBECD prepared by dissolving BM in SBECD/PB Composition 30-2: 0.6 mg/mL BM in 4% SBECD and 0.2% LMWP, prepared by dissolving BM in SBECD/PB, and adding LMWP
Composition 30-3: 0.6 mg/mL BM in 4% SBECD and 1% LMWP, prepared by dissolving BM in SBECD/PB, and adding LMWP
Composition 30-4: 0.6 mg/mL BM in 4% SBECD and 0.2% LMWP, prepared by dissolving LMWP in SBECD/PB, and adding BM
Composition 30-5: 0.6 mg/mL BM in 4% SBECD and 0.2% LMWP, prepared by dissolving LMWP in SBECD/PB, and adding BM.

The compositions were incubated at 25° C., and were periodically analyzed by HPLC as follows. 10 μL samples were separated on HPLC using Waters SymmetryShield RP-18 3.5 μm column (4.6×50 mm) at the flow of 1.5 mL/min of acetonitrile-water gradient containing 0.1% TFA. Peak detection was performed by means of UV absorption detection at 260 nm. The area of the peak of bendamustine was used to evaluate the rate of drug decomposition in the first order kinetics model. The results expressed as decomposition half times (T½) are presented in Table 17 below.

TABLE 17

| Composition | T½ |
|---|---|
| Control: 0.6 mg/mL BM | 44 min |
| Composition 30-1: 4% SBECD, 0.6 mg/mL BM | 642 min |
| Composition 30-2: 4% SBECD, 0.6 mg/mL BM, 0.2% LMWP | 707 min |
| Composition 30-3: 4% SBECD, 0.6 mg/mL BM, 1% LMWP | 789 min |
| Composition 30-4: 4% SBECD, 0.2% LMWP, 0.6 mg/mL BM | 673 min |
| Composition 30-5: 4% SBECD, 1% LMWP, 0.6 mg/mL BM | 729 min |

The results show that LMWP increases the stability of BM in a solution of BM and SBECD. The results also show that the stabilizing effect of LMWP is larger if this compound is added to the pre-prepared mixture of BM and SBECD (Composition 30-3 vs. 30-5, and composition 30-2 vs. 30-4 respectively).

Example 31

Bendamustine Chemical Stability in Plasma

Heparinized human plasma was spiked, 20 μL into 780 μL of plasma, with the following bendamustine (BM) compositions:
Control: 0.6 mg/mL Bendamustine hydrochloride (BM) in water, prepared by dissolving BM in water.
Composition 31-A: 0.6 mg/mL BM in 4% SBECD, prepared by dissolving BM in 4% (w/w) solution of SBECD in water
Composition 31-B: 0.6 mg/mL BM in 8% SBECD, prepared by dissolving BM in 8% (w/w) solution of SBECD in water
Composition 31-C: 0.6 mg/mL BM in 20% SBECD, prepared by dissolving BM in 20% (w/w) solution of SBECD in water
Composition 31-D: 0.6 mg/mL BM in 40% SBECD, prepared by dissolving BM in 40% (w/w) solution of SBECD in water
Composition 31-1: 0.6 mg/mL BM in 4% SBECD and 3% PI2080, prepared by dissolving BM in 4% (w/w) solution of SBECD in water, and adding PI2080
Composition 31-2: 0.6 mg/mL BM in 8% SBECD and 3% PI2080, prepared by dissolving BM in 8% (w/w) solution of SBECD in water, and adding PI2080
Composition 31-3: 0.6 mg/mL BM in 20% SBECD and 3% PI2080, prepared by dissolving BM in 20% (w/w) solution of SBECD in water, and adding PI2080
Composition 31-4: 0.6 mg/mL BM in 40% SBECD and 3% PI2080, prepared by dissolving BM in 40% (w/w) solution of SBECD in water, and adding PI2080

The concentration of bendamustine in plasma after spiking was initially 0.015 mg/mL. The spiked plasma samples were incubated at 37° C. A sample of 50 μL was periodically withdrawn from spiked plasma, and transferred into 200 μL of 100 mM HCl solution in acetonitrile, mixed and centrifuged. 50 μL of the supernatant was diluted 20 times with 95% acetonitrile, then 20 μL of diluted samples were separated on Waters SymmetryShield RP18 3.5 μm column (4.6× 50 mm) using gradient of acetonitrile (0.1% TFA) in water (0.1% TFA), flow 1.5 mL/min. Peak detection was performed by means of fluorescence detection with extinction at 327 nm and emission at 420 nm. The area of the peak of Bendamustine was used to evaluate the rate of drug decomposition in the first order kinetics model. The results expressed as decomposition half times (T½) are presented in Table 18 below.

TABLE 18

| Formulation | T½ in plasma |
|---|---|
| Control: 0.6 mg/mL BM | 123 min |
| Composition 31-A: 0.6 mg/mL BM, 4% SBECD | 134 min |
| Composition 31-B: 0.6 mg/mL BM, 8% SBECD | 137 min |
| Composition 31-C: 0.6 mg/mL BM, 20% SBECD | 174 min |
| Composition 31-D: 0.6 mg/mL BM, 40% SBECD | 242 min |
| Composition 31-1: 0.6 mg/mL BM, 4% SBECD, 3% PI2080 | 182 min |
| Composition 31-2: 0.6 mg/mL BM, 8% SBECD, 3% PI2080 | 251 min |
| Composition 31-3: 0.6 mg/mL BM, 20% SBECD, 3% PI2080 | 297 min |
| Composition 31-4: 0.6 mg/mL BM, 40% SBECD, 3% PI2080 | 302 min |

The results show that PI2080 increases stability of BM in plasma.

The examples and representative species described herein are for illustrative purposes and are not meant to limit the scope of the invention. From the foregoing description, it will be apparent that variations and modifications may be made to the invention described herein to adopt it to various usages and conditions. Such embodiments are also within the scope of the following claims.

What is claimed is:

1. A composition comprising:
   (a) bendamustine; and
   (b) a charged cyclopolysaccharide having one or more anionic groups selected from sulphate and sulphonyl groups.

2. The composition of claim 1 wherein the cyclopolysaccharide is a beta-cyclodextrin.

3. The composition of claim 2 wherein the cyclopolysaccharide is sulphobutyl ether beta-cyclodextrin, sulfopropylated-beta-cyclodextrin or O-sulfated-beta-cyclodextrin.

4. The composition of claim 3 wherein the cyclopolysaccharide is sulphobutyl ether beta-cyclodextrin.

5. The composition of claim 1 wherein the proportion of bendamustine to cyclopolysaccharide is between about 1:12,500 and about 1:25, by weight.

* * * * *